(12) United States Patent
Soman et al.

(10) Patent No.: US 11,278,578 B2
(45) Date of Patent: Mar. 22, 2022

(54) COMBINATION PROBIOTIC COMPOSITIONS AND USES THEREOF

(71) Applicant: Sanzyme Biologies Private Limited, Hyderabad (IN)

(72) Inventors: Raunak Jay Soman, Hyderabad (IN); Venkat Swamy Malisetty, Hyderabad (IN)

(73) Assignee: Sanzyme Biologics Private Limited, Hyderabad (IN)

( * ) Notice: Subject to any disclaimer, the term of this patent is extended or adjusted under 35 U.S.C. 154(b) by 191 days.

(21) Appl. No.: 16/557,273

(22) Filed: Aug. 30, 2019

(65) Prior Publication Data

US 2020/0069744 A1   Mar. 5, 2020

(30) Foreign Application Priority Data

Sep. 2, 2018 (IN) .............................. 201841032444

(51) Int. Cl.

| | | |
|---|---|---|
| *A61K 39/116* | (2006.01) |
| *A61K 39/02* | (2006.01) |
| *A61K 39/07* | (2006.01) |
| *A61K 33/08* | (2006.01) |
| *A61K 33/06* | (2006.01) |
| *A61K 33/14* | (2006.01) |
| *A01N 63/00* | (2020.01) |
| *A01N 65/00* | (2009.01) |
| *A01N 59/08* | (2006.01) |
| *A01N 59/06* | (2006.01) |
| *A61K 35/742* | (2015.01) |
| *A61K 47/24* | (2006.01) |
| *A61K 47/02* | (2006.01) |
| *A61K 47/12* | (2006.01) |

(52) U.S. Cl.
CPC ............ *A61K 35/742* (2013.01); *A61K 47/02* (2013.01); *A61K 47/12* (2013.01); *A61K 47/24* (2013.01); *A61K 33/06* (2013.01); *A61K 33/08* (2013.01); *A61K 33/14* (2013.01); *A61K 39/07* (2013.01); *A61K 39/116* (2013.01)

(58) Field of Classification Search
CPC ........................... A61K 35/742; A23L 33/135
USPC ............ 424/9.1, 9.2, 93.1, 93.3, 93.4, 93.46
See application file for complete search history.

(56) References Cited

U.S. PATENT DOCUMENTS

| | | | | |
|---|---|---|---|---|
| 8,039,006 | B2 * | 10/2011 | Prato ..................... | A61K 35/742 |
| | | | | 424/246.1 |
| 2005/0100535 | A1 * | 5/2005 | Farmer .................. | A61K 38/47 |
| | | | | 424/93.46 |
| 2012/0328571 | A1 * | 12/2012 | Schmidt .................... | A61P 1/12 |
| | | | | 424/93.2 |
| 2016/0192689 | A1 * | 7/2016 | Horn ....................... | A23L 33/22 |
| | | | | 424/439 |
| 2018/0042972 | A1 * | 2/2018 | Gould .................. | A61K 35/742 |
| 2020/0376048 | A1 * | 12/2020 | Magnone .................. | A61P 3/10 |

OTHER PUBLICATIONS

Urgesi, R., et al. European Review for Medical and Pharmacological Sciences, 18:1344-1353, 2014.*

Gian Luigi Marseglia et al.; Efficacy of Bacillus clausii spores in the prevention of recurrent respiratory infections in children: a pilot study; Therapeutics and Clinical Risk Management 2007:3(1) 13-17.

* cited by examiner

*Primary Examiner* — Gary B Nickol
*Assistant Examiner* — Lakia J Jackson-Tongue
(74) *Attorney, Agent, or Firm* — Amin Talati Wasserman LLP; George M. Carrera, Jr.; Valerie Neymeyer-Tynkov

(57) ABSTRACT

Combinations of probiotic compositions are described which are beneficial for human hosts in reducing gas and bloating, stomach acidity, and constipation also capable of boosting the immune capacity. The compositions comprise blends including *B. coagulans, B. subtilis*, and *B. clausii* in combination with magnesium stearate, magnesium hydroxide, and simethicone. The combination probiotic compositions of the present invention behave in a synergistic manner in their nature of action both in-vitro and in-vivo. The combination probiotic compositions of the present invention are also very stable for comparatively greater amounts of time period.

8 Claims, 13 Drawing Sheets

COMBINATION PROBIOTIC COMPOSITIONS AND USES THEREOF

This application claims priority to Indian Provisional application 201841032444, filed on Sep. 2, 2018, which is hereby incorporated by reference herein.

TECHNICAL FIELD

The present invention relates to the field of food, nutritional supplements, and pharmaceuticals. More particularly the present invention relates to the field of beneficial microorganisms for the human host. Further the present invention pertains to probiotic compositions and combinations thereof intended for human hosts.

BACKGROUND

Probiotics are defined as live microbial food supplements that benefit the host by improving the intestinal microbial balance. Resident bacteria serve a central line of resistance to colonization by exogenous microbes and thus assist in preventing the potential invasion of the intestinal mucosa by an incoming pathogen. The protective function is known as the barrier effect or colonization resistance, and the bacteria have a number of important roles. Adherent nonpathogenic bacteria can often prevent attachment and subsequent entry of suspected pathogens into epithelial cells. Commensal bacteria compete for available nutrients in ecological niches and, in doing so, maintain the collective microenvironment by administering and consuming all resources. This mutual and beneficial relationship helps dampen unwanted overproduction of nutrients, which could potentially support intrusion of microbial competitors that could have a pathogenic outcome for the host. The microflora also makes an important metabolic contribution to the synthesis of certain vitamins.

The function of a particular single probiotic bacterial strain has been acknowledged in the art to be highly personalized, meaning thereby each different individual would experience different levels of comfort and relief through a given particular probiotic composition containing most of the time only a single bacterial strain. Thus probiotics have varying effects on different individuals and the beneficial effects are subject to finding the right bacterial strain for a particular individual. In view of such specificity of bacterial strains for each separate individual or group of people, it is almost impossible to find the right probiotic strain for each separate individual. Therefore, a combination of different bacterial strains within a single composition is expected to provide a solution to such probiotic specificity wherein availability of different bacterial strains within a single composition would probably increase the chances to maximize the beneficial effects of probiotics across all geographic locations.

There are some technical pre-requisites to consider combination probiotic bacterial compositions. Selection of the appropriate bacterial strains which is inherently found in the gastro-intestinal tract of humans is always preferable. It would also be advantageous to include such bacteria which are known to be effective against multiple physiological indications related to the digestive system such as gas, acidity, constipation or diarrhea. However, selection of multiple bacterial strains in a single probiotic composition should also be compatible with each other. The existence of multiple bacterial strains must not experience biological interference to avoid reduction in the count of any one of the bacterial strains due to dominance of other bacterial strains. Sometimes, none of the different bacterial strains may seem to co-exist at all with the other bacterial strains in a single composition owing to their various natural characteristics for example, settling in different regions of the human digestive tract, respiratory mechanisms of each different bacteria, other physico-chemical characteristics of each individual bacterial strain. The number of bacterial strains must be limited and optimized and unnecessary addition of more and more bacterial strains should be avoided. It has also been proved that overloading of different strains fail to show any beneficial activity at all. Obviously such combination probiotic composition must be free from all kinds of side effects, and enabled to release themselves at desirable locations of the GI tract to considerably higher counts without getting inactive or killed due to exposure to several extreme changes in pH along the entire digestive system of humans.

Generally, any combination probiotic contains the spores of the bacteria to increase their shelf life and stability as a commercial composition. Yet, the exposure of the probiotic spores to the harsh stomach environment has always been questioned with respect to conversion of the spores to their respective vegetative forms inside the respective locations of the human gastro-intestinal tract thereby causing only a nominal amount of bacterial activity. To avoid this situation, recent state of the art has proposed availability of probiotics encapsulated in a synthetic coating or wax coating supplemented with hydrophilic and hydrophobic agents that contains the vegetative form of the said bacteria to sustained release as well as protection against exposure to acidic environments. However, such encapsulated methods have their own disadvantages related to killing of the probiotics due to incompatible synthetic coatings and increase in the moisture content of the entire probiotic composition ultimately reducing the shelf life of the probiotic composition (thus also requiring cold-chain transport of the probiotics) and resulting in loss of efficacy of such probiotic compositions. At the same time, economic considerations such as the product need not be refrigerated, are also equally important to provide a more cost-effective pro-biotic product. Hence, new compositions of combination probiotics that overcomes these concerns are desirable. Such compositions are preferably to be in the vegetative form of the bacteria yet stable enough to withstand both environmental changes and body's internal requirements.

Constipation is one of the most commonly occurring problems that is more common across the World especially in the Western countries where protein and fat intake may exceed the intake of nutritional fibers. Fibers are available from green leafy vegetables. But, present lifestyle habits ultimately leaves people without having specific attention on a balanced diet that includes the source of pre-biotic intake for supplementing the growth of our healthy bacteria in our digestive tract. Prebiotics are known as those essential components which acts as a nutrient for all the probiotics in the gastro-intestinal tract.

Drinking plenty of water is another means to combat the issue of constipation which is actually caused by dehydration. Loss of water intake causes excess of water absorption from the food in the digestive tract, thereby making the stool very hard to pass by and hence resulting into Irritable Bowel Syndrome. It is known the art that probiotics help in fighting irritable bowel syndrome. Probiotics are known to replace pathogenic bacteria, and help in digestion of nutrients from food. However, present lifestyle disorders such as diabetes, blood pressure or the like, etc, leaves several side effects which might adversely affect the probiotic population in the human digestive tract. Exposure to strong antibiotics ends up in reduction of total good bacteria as well while killing the pathogens. This results in a greater problem of constipation due to the decrease in the number of probiotic population as a result of an irregular diet aided with excessive medication.

Formation of gas in the abdomen is another common health hazard in humans. Over eating, improper diet avoiding chewing, stress and lack of exercise are some of the very common reasons to catalyze the formation of gas, bloating and eventually diarrhea. Lot of medications are available to reduce formation of gas, but they are either ineffective or exposes the body to further strong chemicals which again reduces the probiotic population. It is advisable to solve this problem naturally. Therefore, it is advantageous to involve the role of probiotics in reducing abdominal gas and bloating as well.

Newer combination probiotics having the capacity to reduce gas and related problems as a natural supplement is desirable. Recently, probiotic bacteria *Bacillus coagulans* have shown to be effective in gas reduction in healthy adults. *Bacillus clausii* has been studied to reduce diarrhea and antibiotic associated diarrhea. *Bacillus clausii* is a probiotic that is also capable of modulating the immune response. *B. clausii* also helps to stimulate the immune system by promoting Th1 and T regulatory (Treg) immunity, and by decreasing Th2 activity (G. Ciprandi, et al., *Eur. Ann. Allergy Clin. Immunol.* (2005) 37:129-33). Specifically, it has been demonstrated that *B. clausii* stimulates Th1 and Treg immunity, promoting IL-12, IFN-γ, IL-10, and transforming growth factor-beta (TGF-β) synthesis, and down-regulates Th2 response, inhibiting IL-4 production (G. Ciprandi, et al., *Ped. Allergy Immunol.* (2004) 15:148-51). Inventors of the present invention has developed new combination probiotic compositions those are helpful in combating the recurring issues of constipation, diarrhea, irritable bowel syndrome along with boosting the immunity against common infections. The new probiotic compositions proposed by the present invention takes care of metabolic requirements related to a complete balanced nutritious diet. Additionally, these combinations are proved to be beneficial for the human digestive system and most importantly have been experimentally shown to work in an effective and synergistic manner which is absent in any other known probiotic compositions available to date.

SUMMARY

In one embodiment, a probiotic blend composition includes *B. coagulans, B. subtilis*, and *B. clausii* in combination with magnesium stearate, magnesium hydroxide, and simethicone. In the probiotic blend composition of the present invention, the amount of *B. coagulans* is between about 0.1 billion to about 1.5 billion CFUs, the amount of *B. clausii* between about 0.1 billion to about 0.5 billion CFUs, and the amount of *B. subtilis* is between about 0.1 billion to about 1.5 billion CFUs.

In another embodiment, a method for improving digestion of complex carbohydrates, proteins and fibers in a human includes the steps of providing a probiotic blend composition comprising *B. coagulans, B. subtilis*, and *B. clausii* in combination with magnesium stearate, magnesium hydroxide, and simethicone, and orally administering to the human the probiotic blend composition in such a manner that beneficial effects are realized.

In another embodiment, a method for increasing the probiotic population in the digestive system of a human includes the steps of providing a probiotic blend composition comprising *B. coagulans, B. subtilis*, and *B. clausii* in combination with magnesium stearate, magnesium hydroxide, and simethicone, and orally administering to the human the probiotic blend composition in such a manner that beneficial effects are realized.

One more embodiment of the invention includes a method for treating or preventing a condition in a human selected from the group consisting of Irritable Bowel Syndrome (IBS), diarrhea, bloating, formation of abdominal gas, constipation, bowel irregularity, and reactions to antibiotic treatment, comprising the steps of providing a probiotic blend composition comprising *B. coagulans, B. subtilis*, and *B. clausii* in combination with magnesium stearate, magnesium hydroxide, and simethicone; and administering to the human the probiotic blend composition.

The primary objective of the invention is to provide a combination probiotic composition.

One objective of the invention is to provide a combination probiotic composition wherein the said combination of probiotics is capable of health benefits to a large scale of human population obviating the need of specific probiotic strains for different individuals.

Another objective of the invention is to provide a combination probiotic composition comprising at least three different bacterial strains without showing any inter-bacterial competition or interference both in-vitro and in-vivo.

One more objective of the invention is to provide a combination probiotic composition which is capable of digestion of left-out complex undigestible components in the food such as alcohols, large chain polysaccharides or other fats.

Another objective of the invention is to provide an effective combination probiotic composition which is helpful in preventing constipation, diarrhea and gas formation in the stomach.

Further, another objective of the invention is to provide a combination probiotic composition which is also helpful in increasing the immune capacity as well.

Among others, yet another objective of the invention is to provide a combination a probiotic composition that is present in the form of spores of the bacterial strains, without any synthetic or wax coating, and that is at the same time very stable in nature without loss of potency for at least 3 years at given temperature ranges.

It is also yet another objective of the invention that the said combination probiotic composition of the present invention possesses synergistic effect in the mode of its functionality as well as existence in a single mixed blend in-vitro as well.

DETAILED DESCRIPTION

Figure 1A:
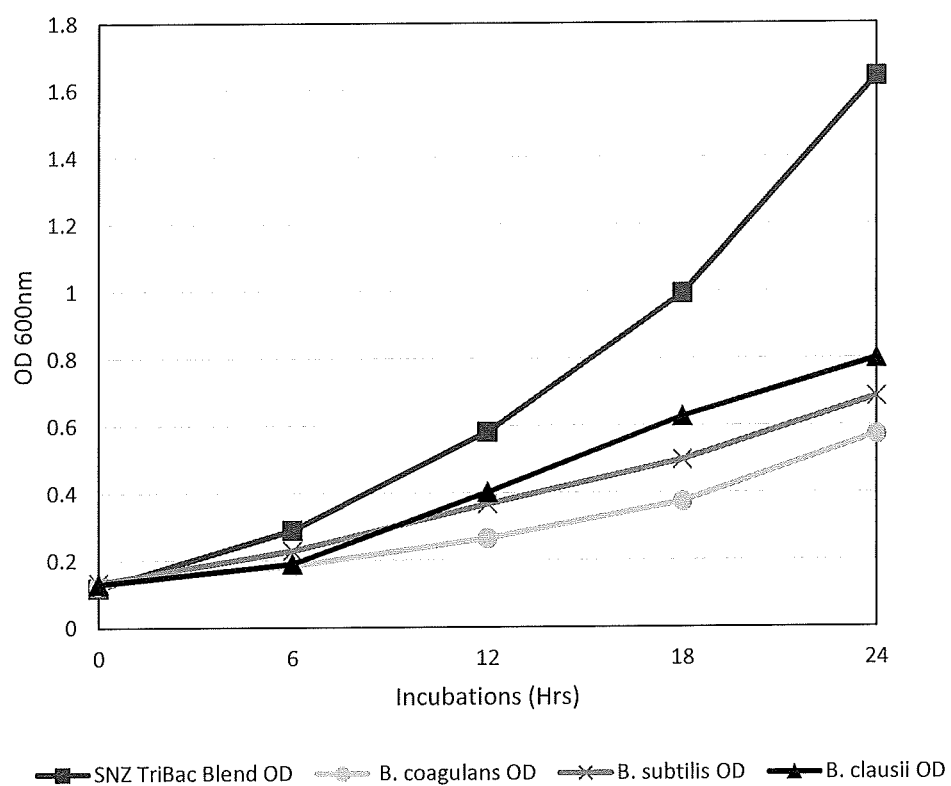
FIG. 1A depicts a Growth profile of a Combination probiotic composition (SNZ TriBac Blend) and individual strains of formulation through spectrophotometric OD600 method.

Many disorders of the gut have been associated with a disturbance in the distribution of bacterial community in the intestine. Inflammatory bowel disease, intestinal gas, constipation and diarrhea are believed to be correlated with an imbalance in gut ecology favoring the growth of pathogenic strains. There is good clinical evidence showing that the intestinal microbial flora have a central role in maintaining both the health and well being of humans. Thus probiotic dietary supplement can be an effective therapy against gastrointestinal symptoms in adults with post-prandial intestinal gas-related symptoms (abdominal pain, distention, flatulence) but no gastrointestinal (GI) diagnoses to explain the symptoms.

It has been generally accepted that probiotic products intended for the benefit of more than one condition are likely to be more effective as multiple strains than single strain products. Inventors of the present invention have developed an effective combination of *Bacillus subtilis* and *Bacillus clausii* bacteria to optimize the health of the small and large intestines, further also including a *Bacillus coagulans* strain which assists in regulating the often neglected transient flora. The strains *Bacillus coagulans* SNZ 1969 is assigned by FDA as GRAS (Generally Recognized As Safe) substance. *Bacillus clausii* has safe history of usage from children to adults in different ailments of gastrointestinal tract. *Bacillus subtilis* SNZ 1972 and *Bacillus clausii* SNZ 1971 are self affirmed generally recognized as safe technically established by the applicant.

*Bacillus coagulans* is potent in fighting inflammatory conditions, helps in digestion and prevent the growth of harmful bacteria. *B. coagulans* has the unique ability of producing lactic acid. *B. coagulans* also plays a key role in digestion of food components and absorption of nutrients. *Bacillus clausii* is the largest selling probiotic in the world. *Bacillus clausii* is recommended for use during antibiotic treatment due to its ability to resist damage caused by various antibiotics. It is a powerful supplement that can be used in adjunct with antibiotic therapy to keep the organisms balanced in the gut. *Bacillus subtilis* produce many antibiotics to fight against opportunistic and harmful bacteria. It has the ability to prevent growth of harmful bacteria in a variety of conditions. *Bacillus subtilis* also produces a number of other nutrients that have systemic health benefits such as vitamins B complex and vitamin K2.

As used herein, an "effective amount" or an "amount effective for" is defined as an amount effective, at dosages and for periods of time necessary, to achieve a desired biological result, such as reducing, preventing, or treating a disease or condition and/or inducing a particular beneficial effect. The effective amount of compositions of the disclosure may vary according to factors such as age, sex, and weight of the individual. Dosage regime may be adjusted to provide the optimum response. Several divided doses may be administered daily, or the dose may be proportionally reduced as indicated by the exigencies of an individual's situation. As will be readily appreciated, a composition in accordance with the present disclosure may be administered in a single serving or in multiple servings spaced throughout the day. As will be understood by those skilled in the art, servings need not be limited to daily administration, and may be on an every second or third day or other convenient effective basis. The administration on a given day may be in a single serving or in multiple servings spaced throughout the day depending on the exigencies of the situation.

As used herein, the term "subject" or "individual" refers to any vertebrate including, without limitation, humans and other primates (e.g., chimpanzees and other apes and monkey species), farm animals (e.g., cattle, sheep, pigs, goats, and horses), domestic animals (e.g., dogs and cats), laboratory animals (e.g., rodents such as mice, rats, and guinea pigs), and birds (e.g., domestic, wild, and game birds such as chickens, turkeys, and other gallinaceous birds, ducks, geese, and the like). In some implementations, the subject may be a mammal. In other implementations, the subject may be a human.

However, as enumerated earlier, a mixture of three different bacterial strains in a probiotic blend, fight for survival and may inhibit one another and decrease each other's growth, thereby decreasing health benefits since symbiosis is not common among bacteria. It is surprising that the particular probiotic blend of the combination probiotic composition of the present invention showed unique synergistic effect together establishing the symbiotic relation among strains and other beneficial effects as well.

In one embodiment, the present invention provides a combination probiotic composition comprising:
(a) *Bacillus coagulans*;
(b) *Bacillus subtilis*;
(c) *Bacillus clausii*;
(d) Magnesium stearate;
(e) Magnesium hydroxide; and
(f) Simethicone.

One or more pharmaceutical or nutraceutical carriers may be used. The probiotic microorganism may be in the form of spores or in a vegetative state.

SNZ 1969 is a strain of *Bacillus coagulans*, a preparation of which is manufactured by Sanzyme Biologics Pvt. Ltd., Hyderabad, India. *Bacillus coagulans* SNZ 1969 was deposited on Dec. 6, 2012 with the Microbial Type Culture Collection & Gene Bank, CSIR-Institute of Microbial Technology, Sector 39-A (Chandigarh, India 160 036) under the accession number MTCC 5724.

SNZ 1972 is a strain of *Bacillus subtilis*, a preparation of which is manufactured by Sanzyme Biologics Pvt. Ltd., Hyderabad, India. *Bacillus subtilis* SNZ 1972 was deposited on Mar. 13, 2015 with the Microbial Type Culture Collection & Gene Bank, CSIR-Institute of Microbial Technology, Sector 39-A (Chandigarh, India 160 036) under the accession number MTCC 5981.

SNZ 1971 is a strain of Bacillus clausii, a preparation of which is manufactured by Sanzyme Biologics Pvt. Ltd., Hyderabad, India. *Bacillus clausii* SNZ 1971 was deposited on Dec. 16, 2014 with the Microbial Type Culture Collection & Gene Bank, CSIR-Institute of Microbial Technology, Sector 39-A (Chandigarh, India 160 036) under the accession number MTCC 5980.

In one embodiment, the spore-containing compositions may or may not contain one or more of the above bacterial species, and yet said compositions may be used to increase the growth of those protective, beneficial bacterial populations by adding the spore-containing composition, thus increasing the overall microbiome diversity.

The present invention is briefly described in the form of following embodiments only for the purpose of exemplifying the nature and ambit of the invention. The person skilled in the art would appreciate that mere variations or differences in the following nature of experiments and compositions thereof would not invariably differentiate from the present invention, and thereby fall under the scope and ambit of the present invention as long as such variations or changes so done is with an intent to merely perform mere incidental changes to the working examples as provided below.

Probiotics are measured by colony forming units ("CFUs") and can be measured as CFUs/g or CFUs/vol. Alternatively, a given probiotic dosage can be delivered as a total in CFUs. Few studies have been done to determine effective dosages, but effective dosages are usually in the hundreds of millions of CFUs or higher. If probiotics are being used to help with digestion, probiotics should be taken with meals, but otherwise the probiotics may survive better if taken between meals, particularly if taken with liquids that help to dilute stomach acid and move the probiotics more quickly into the digestive tract. Probiotics may be given short-term or long-term.

In some implementations, the concentration of the probiotic microorganism in the composition may be at least about $1 \cdot 10^9$ CFU/g (or per dose), at least about $2 \cdot 10^9$ CFU/g, at least about $3 \cdot 10^9$ CFU/g, at least about $4 \cdot 10^9$ CFU/g, at least about $5 \cdot 10^9$ CFU/g, at least about $6 \cdot 10^9$ CFU/g, at least about $7 \cdot 10^9$ CFU/g, at least about $8 \cdot 10^9$ CFU/g, at least about $9 \cdot 10^9$ CFU/g, at least about $1 \cdot 10^{10}$ CFU/g, at least about $2 \cdot 10^{10}$ CFU/g, at least about $3 \cdot 10^{10}$ CFU/g, at least about $4 \cdot 10^{10}$ CFU/g, at least about $5 \cdot 10^{10}$ CFU/g, at least about $6 \cdot 10^{10}$ CFU/g, at least about $7 \cdot 10^{10}$ CFU/g, at least about $8 \cdot 10^{10}$ CFU/g, at least about $9 \cdot 10^{10}$ CFU/g, or at least about $1 \cdot 10^{11}$ CFU/g.

The spore-based probiotic supplement may comprise spores having a survival rate within any of the following ranges after exposure to gastric acid in situ: about 75% to about 99%, about 80% to about 95%, about 85% to about 90%, and greater than about 90%.

The spore-based probiotic supplement may comprise a number of spores within any of the following ranges: at least 0.1 billion to about 10 billion spores, about 1.5 billion spores to about 9.5 billion spores, about 2 billion spores to about 9 billion spores, about 2.5 billion spores to about 8 billion spores, about 3 billion spores to about 7 billion spores, about 3.5 billion spores to about 6.5 billion spores, about 3.5 billion spores to about 6 billion spores, about 3.5 billion spores to about 5 billion spores, and about 3.5 billion spores to about 4.5 billion spores.

The spore-based probiotic supplement may comprise a liquid, confectionary item, powder or pill form or may be added to a food product. In one implementation, about $1 \cdot 10^{10}$ CFU of microorganism is present in each gram of bulk, dried raw powder where each gram contains about 60% or less of bacterial mass and about 40% carrier system. In other implementations, each gram contains about 70% or less of bacterial mass and about 30% carrier system, about 80% or less of bacterial mass and about 20% carrier system, about 90% or less of bacterial mass and about 10% carrier system, about 50% or less of bacterial mass and about 50% carrier system, about 40% or less of bacterial mass and about 60% carrier system, about 30% or less of bacterial mass and about 70% carrier system, about 20% or less of bacterial mass and about 80% carrier system, or about 10% or less of bacterial mass and about 90% carrier system. For this disclosure, a carrier means a chemical additive or excipient in addition to the chemical components used in the probiotic blend composition, i.e., in addition to magnesium stearate, magnesium hydroxide, and simethicone.

Implementations of the methods and compositions disclosed herein may comprise a spore-based probiotic. A spore-based probiotic is comprised of endospores which are highly resistant to acidic pH, are stable at room temperature, and deliver a much greater quantity of high viability bacteria to the small intestine than traditional probiotic supplements. Traditional micro-encapsulation uses live microorganisms which are then micro-encapsulated in an effort to protect the microorganisms; however, this is a process that inherently leads to the eventual death of the microorganisms thereby reducing the efficacy of the microorganisms. Using spore-based microorganisms that have been naturally microencapsulated to form endospores may be preferable as these microorganisms are dormant and do not experience a degradation in efficacy over time. These spore-based microorganisms are also particularly thermally stable and can survive UV pasteurization, so they are also able to be added to food products or beverages prior to thermal exposure or UV pasteurization without experiencing a degradation in efficacy over time.

EXAMPLE 1

Synergistic Growth Efficiency of Combination Probiotic Composition

To check the synergy, bacterial strains *B. coagulans, B. subtilis* & *B. clausii* were separately grown individually and also as a combination of 3 bacterial strains in a blend (termed as "SNZ TriBac" or "TriBac" hereafter) at equal potency in presence of the same working medium. TriBac may be formulated with or without chemical components as shown above (magnesium stearate, magnesium hydroxide, and simethicone) along with the bacterial strains *Bacillus coagulans* SNZ 1969, *Bacillus subtilis* SNZ 1972, *Bacillus clausii* SNZ 1971 available from Sanzyme Biologics Pvt.

Figure 1B:
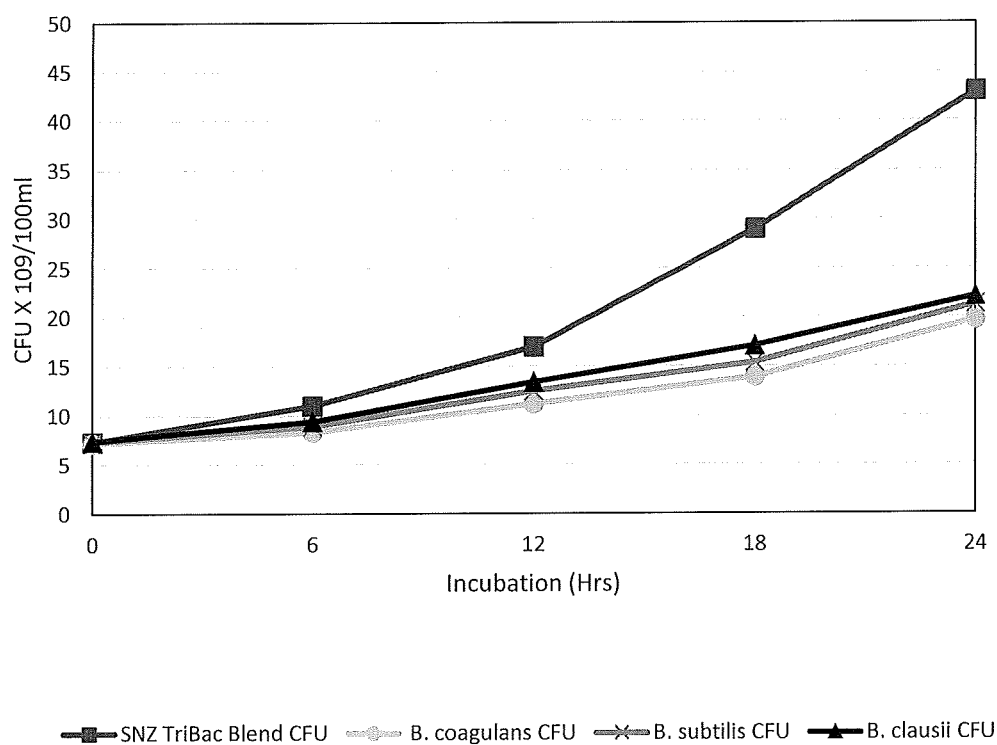
FIG. 1B depicts a growth profile of Combination probiotic composition (SNZ TriBac Blend) and individual strains of formulation through plate count method.

Ltd., Hyderabad, India (see, Table 10). The growth was observed based on OD value and plate count method. Spectrophotometric $OD_{600}$ data gives total no. of viable & dead cells in the culture while plate count method specifically shows count of viable cells. The curve showed the highest growth efficiency as blend as compared to individual strains by both the methods (OD method as depicted in FIG. 1A and plate count method as depicted in FIG. 1B) thus showing synergy among the strains as a blend.

Figure 2:
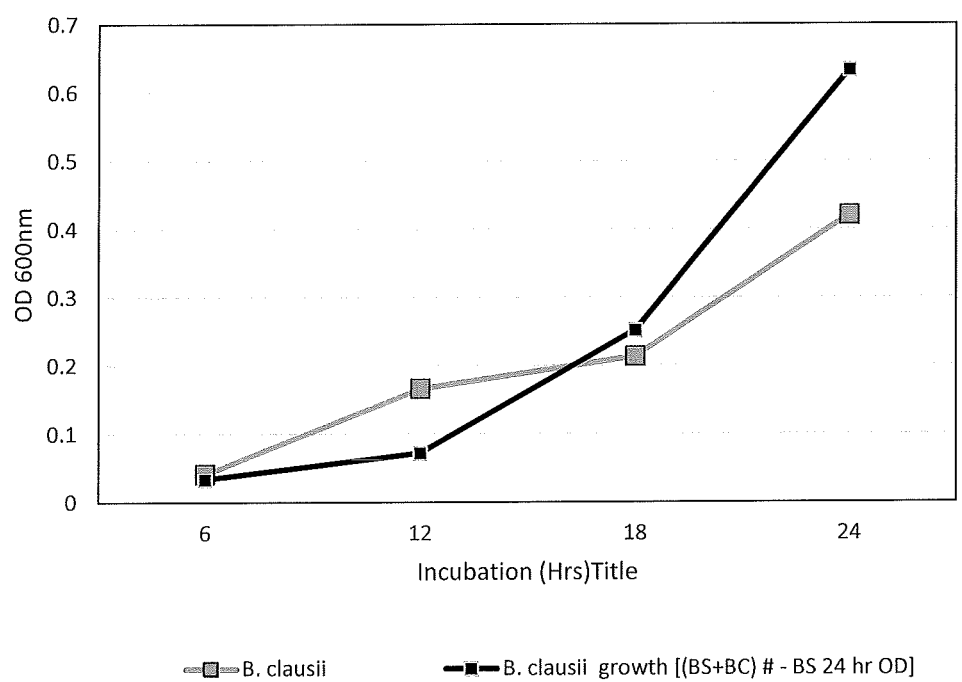
FIG. 2 depicts a Synergistic effect in growth of *B. clausii* in a media previously grown with *B. subtilis* and killed through autoclaving prior to inoculation with *B. clausii*. For *B. clausii* growth [(BS+BC)#-BS 24 hr OD], BS refers to *B. subtilis*, BC refers to *B. clausii*.

Table 1 shows a growth profile of individual strains and a combination probiotic composition of SNZ TriBac™ (equal potency) based on spectrophotometric readings and plate count.

as compared to *B. clausii* strain growing alone. Thus *B. clausii* SNZ 1971 grows significantly better in a medium that was pre inoculated with *B. subtilis* SNZ 1972 showing better availability of nutrients, growth factors and synergy between the combination of bacterial strains (FIG. 2).

EXAMPLE 3

Digestion Capacity of Foods Rich in Protein & Fibers by the Combination Probiotic Composition of the Present Invention In natural conditions we all know that all probiotics have to thrive in human gut. They will be receiving all the

TABLE 1

| | Growth profile (OD at 600 nm) | | | | Growth profile (Billion CFU/100 ml) | | | |
|---|---|---|---|---|---|---|---|---|
| | Combination probiotic composition | *B. coagulans* | *B. subtilis* | *B. clausil* | Combination probiotic composition | *B. coagulans* | *B. subtilis* | *B. clausii* |
| | | | | Potency | | | | |
| Hrs | 2 Billion | 2 Billion | 2 Billion | 2 Billion | 2 Billion | 2 Billion | 2 Billion | 2 Billion |
| 6 | 0.290 | 0.184 | 0.229 | 0.190 | 11 | 8.3 | 8.9 | 9.4 |
| 12 | 0.582 | 0.265 | 0.367 | 0.403 | 17 | 11.2 | 12.5 | 13.4 |
| 18 | 0.995 | 0.374 | 0.499 | 0.628 | 29 | 13.9 | 15.4 | 17.1 |
| 24 | 1.641 | 0.573 | 0.686 | 0.8 | 43 | 19.7 | 21.3 | 22.1 |

Conclusion

As shown in Table 1, the spectrophotometric readings and colony count of the combination probiotic composition comes to at least double (objectively 2.05X count for OD and 1.95X for CFU wherein 'X' is the maximum growth attained by any one of the bacteria present individually after 24 hours) showing synergy among strains in growth and therefore these strains do not inhibit each other.

EXAMPLE 2

Synergistic Effect of Growth of *B. clausii* in Presence of *B. subtilis* and *B. coagulans*

Each bacteria has different growth requirements. Bacteria can grow properly once they get utilizable nutrients. The bacteria in combination helps in digestion of complex nutrients into simpler forms and make it available for slow growers to establish faster. *B. clausii* is known to be unable to digest, or very poor in digestion of complex proteins. *B. clausii* needs simpler proteins for its proper growth while *B subtilis* has a robust growth and breaks down complex proteins so that simpler proteins are subsequently made available to *B. clausii* for its growth which is evident as shown in FIG. 2.

The synergistic effect of the combination of strains helps in enhancing the growth of slow growing strains like *B. clausii* by increasing nutrient availability of simple proteins in simplified form which otherwise can't be utilized by *B. clausii* (slow growing strain). Growth of *B. clausii* was enhanced when it was grown in a medium previously grown with *B. subtilis* and therefore utilized the nutrients in the simpler form available in the media that was previously grown with *B. subtilis*. Prior to inoculation of *B. clausii* SNZ 1971, *B. subtilis* SNZ 1972 was killed by autoclave so that it should not be accounted in the final growth of *B. clausii*. In this experiment *B. clausii* (alone) and *B. clausii* combined with *B. subtilis* (killed) were grown separately for 24 hrs. OD was measured at defined intervals. It was observed the killed *B. subtilis* cells helped *B clausii* cells to grow better nutrients required for growth through the food we consume. So it would be important to understand whether synergy will also help in survival on different food substrates that are native to peoples' diets and the bacteria can utilize these food substrates to grow and proliferate. As we all know probiotics helps in digestion of complex foods rich in proteins & fibres. The experiment was designed to show the efficacy of combination probiotic over digestion of vegetable and non-vegetable based foods like Pigeon pea (i.e., Tur dal, rich in protein), Spinach (rich in fibers), meat powder and wheat flour.

3A. Pigeon Pea or Tur Dal

Cooked Pigeon Pea 3% with 1% dextrose was taken as an experimental medium. 2 billion potencies of each organism was inoculated into the medium and incubated for 24 hrs. During the incubation, samples were withdrawn at the interval of 6, 12, 18 and 24 hrs and checked for OD measurement at 600 nm ($OD_{600}$) and CFU count.

Figure 3A:
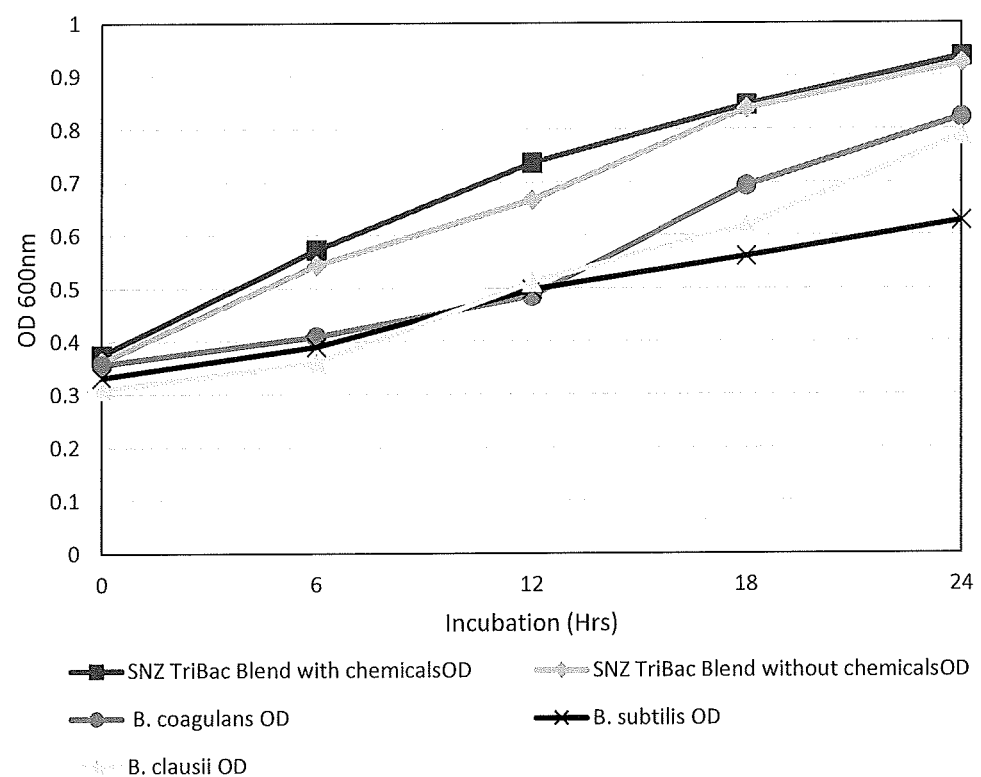
FIG. 3A depicts Comparative growth (at OD600) for SNZ TriBac Blend (with and without chemicals) as against individual strains for digestion of Tur Dal based media.

Table 2 shows the Growth profile at $OD_{600}$ of combination TriBac blend in comparison with individual bacteria for digestion of Pigeon Pea based media (corresponding FIG. 3A).

TABLE 2

| | TriBac blend with Chemicals | TriBac blend without Chemicals | *B. coagulans* | *B. subtilis* | *B. clausii* |
|---|---|---|---|---|---|
| | | | Potency | | |
| Hrs | 2 Billion | 2 Billion | 2 Billion | 2 Billion | 2 Billion |
| 6 | 0.573 | 0.544 | 0.409 | 0.390 | 0.359 |
| 12 | 0.737 | 0.667 | 0.486 | 0.498 | 0.512 |
| 18 | 0.846 | 0.839 | 0.694 | 0.561 | 0.618 |
| 24 | 0.937 | 0.924 | 0.823 | 0.627 | 0.788 |

Figure 3B:
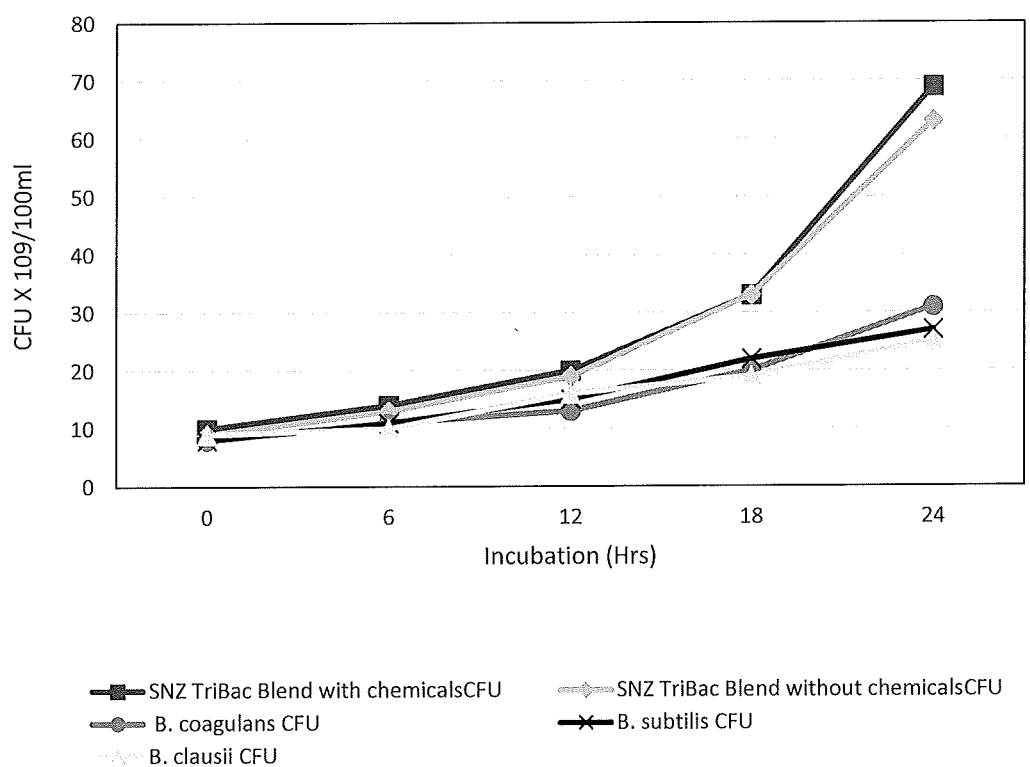
FIG. 3B depicts Comparative growth (through plate count CFU/ml) for SNZ TriBac Blend (with and without chemicals) as against individual strains for digestion of Tur Dal based media.

Table 3 shows the Growth profile (billion CFU/ 100 ml) of combination TriBac blend in comparison with individual bacteria for digestion of Tur Dal based media (corresponding FIG. 3B). As shown in Table 3, the colony count of the combination probiotic composition with the chemicals is at least double (objectively 2.23X count for CFU wherein 'X' is the maximum growth attained by any one of the bacteria (herein *Bacillus coagulans* SNZ 1969 present individually after 24 hours) showing synergy among strains in growth.

TABLE 3

| Hrs | TriBac blend with Chemicals | TriBac blend without Chemicals | *B. coagulans* Potency | *B. subtilis* | *B. clausii* |
|---|---|---|---|---|---|
| | 2 Billion | 2 Billion | 2 Billion | 2 Billion | 2 Billion |
| 6 | 14 | 13 | 11 | 11 | 10 |
| 12 | 20 | 19 | 13 | 15 | 16 |
| 18 | 33 | 33 | 20 | 22 | 19 |
| 24 | 69 | 63 | 31 | 27 | 25 |

3B. Wheat Flour

Wheat flour 3% with 1% sugar was taken as an experimental medium. 2 billion potencies of each organism was inoculated into the medium and incubate for 24 hrs. During the incubation, samples were withdrawn at the interval of 6, 12, 18 and 24 hrs and proceed further for OD measurement at 600 nm and CFU count.

Figure 4A:
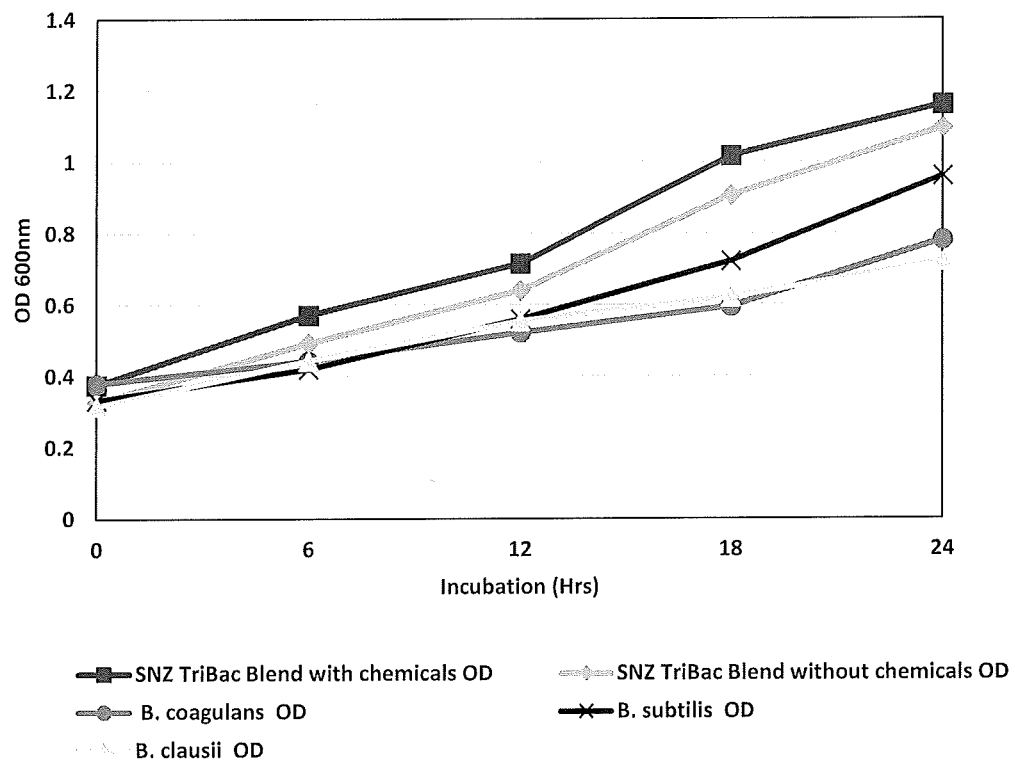
FIG. 4A depicts Comparative growth (at OD600) for SNZ TriBac Blend (with and without chemicals) as against individual strains for digestion of Wheat based media.

Table 4 shows the Growth profile ($OD_{600}$) of combination TriBac blend in comparison with individual bacteria for digestion of Wheat flour based media (corresponding FIG. 4A).

TABLE 4

| Hrs | TriBac blend with Chemicals ($OD_{600}$) | TriBac blend without Chemicals | *B. coagulans* Potency | *B. subtilis* | *B. clausii* |
|---|---|---|---|---|---|
| | 2 Billion | 2 Billion | 2 Billion | 2 Billion | 2 Billion |
| 6 | 0.571 | 0.492 | 0.442 | 0.419 | 0.443 |
| 12 | 0.715 | 0.640 | 0.522 | 0.559 | 0.554 |
| 18 | 1.017 | 0.905 | 0.594 | 0.722 | 0.620 |
| 24 | 1.160 | 1.095 | 0.781 | 0.959 | 0.720 |

Figure 4B:
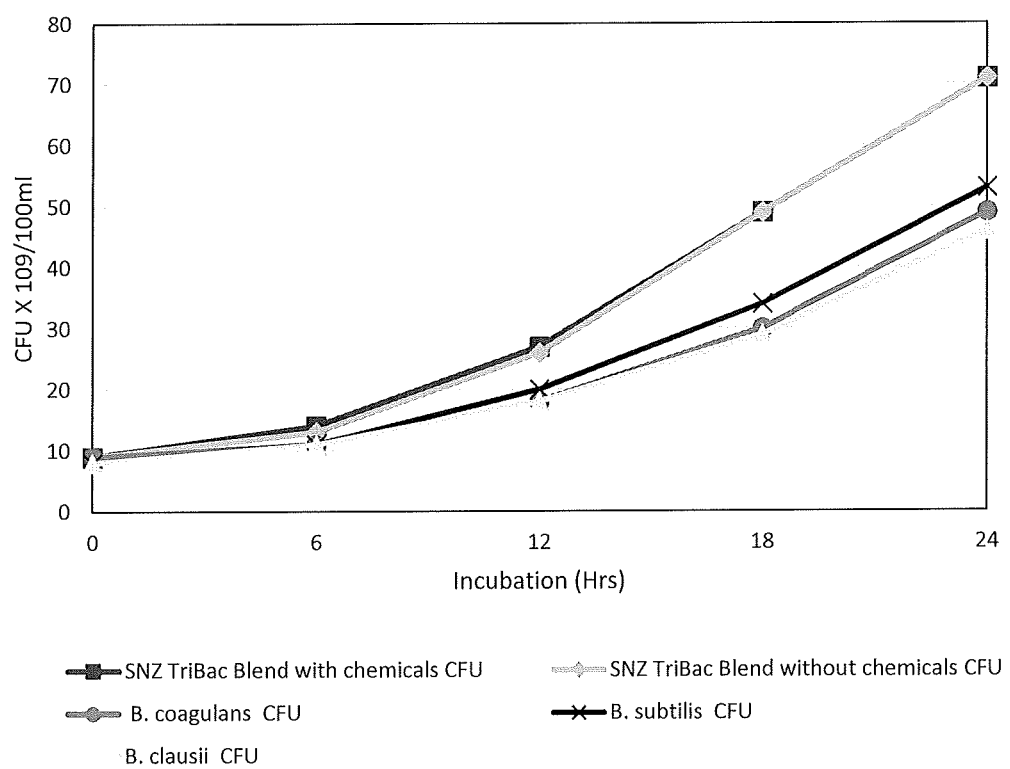
FIG. 4B depicts Comparative growth (plate count CFU/ml) for SNZ TriBac Blend (with and without chemicals) as against individual strains for digestion of Wheat based media.

Table 5 shows the Growth profile (billion CFU/100 ml) of combination TriBac blend in comparison with individual bacteria for digestion of Wheat based media (corresponding FIG. 4B). As shown in Table 5, the colony count of the combination probiotic composition with the chemicals is 1.34X count for CFU wherein 'X' is the maximum growth attained by any one of the bacteria (herein *Bacillus subtilis* SNZ 1972 present individually after 24 hours) showing synergy among strains.

TABLE 5

| Hrs | TriBac blend with Chemicals | TriBac blend without Chemicals | *B. coagulans* Potency | *B. subtilis* | *B. clausii* |
|---|---|---|---|---|---|
| | 2 Billion | 2 Billion | 2 Billion | 2 Billion | 2 Billion |
| 6 | 14 | 13 | 11 | 11 | 11 |
| 12 | 27 | 26 | 18 | 20 | 18 |
| 18 | 49 | 49 | 30 | 34 | 29 |
| 24 | 71 | 71 | 49 | 53 | 46 |

3C. Meat Powder (Beef Extract)

Figure 5A:
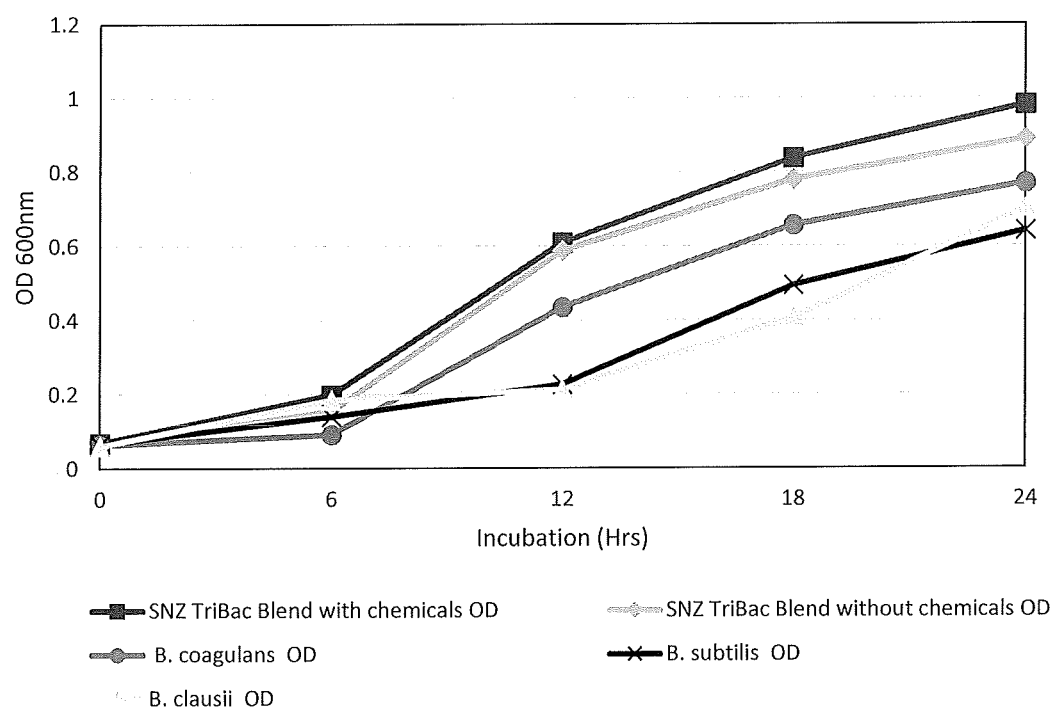
FIG. 5A depicts Comparative growth (at OD600) for SNZ TriBac Blend (with and without chemicals) as against individual strains for digestion of Meat based media.
Figure 5B:
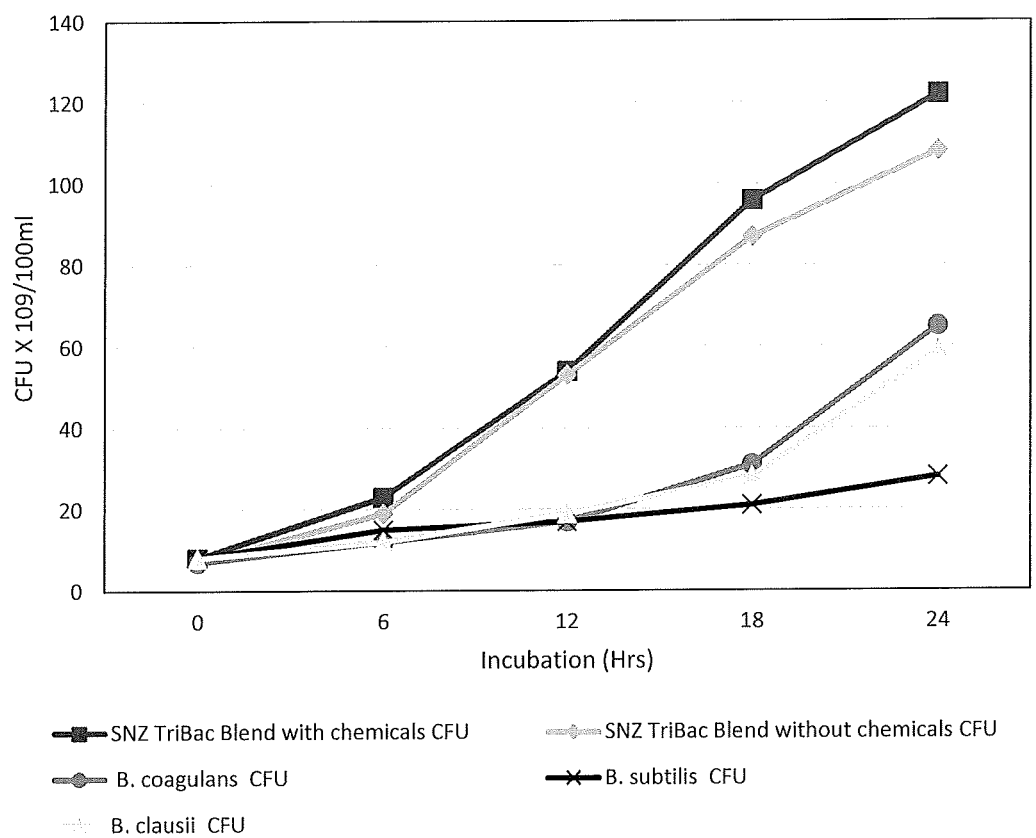
FIG. 5B depicts Comparative growth (plate count CFU/ml) for SNZ TriBac Blend (with and without chemicals) as against individual strains for digestion of Meat based media.

Meat powder 3% with 1% sugar was taken as an experimental medium. 2 billion potencies of each organism was inoculated into the medium and incubate for 24 hrs. During the incubation, samples were withdrawn at the interval of 6, 12, 18 and 24 hrs and proceed further for OD measurement at 600 nm (Table 6, FIG. 5A) and CFU count. (Table 7, in terms of billion CFU/100 ml; FIG. 5B).

TABLE 6

| Hrs | TriBac blend with Chemicals ($OD_{600}$) | TriBac blend without Chemicals | *B. coagulans* Potency | *B. subtilis* | *B. clausii* |
|---|---|---|---|---|---|
| | 2 Billion | 2 Billion | 2 Billion | 2 Billion | 2 Billion |
| 6 | 0.198 | 0.154 | 0.091 | 0.140 | 0.185 |
| 12 | 0.610 | 0.588 | 0.435 | 0.227 | 0.212 |
| 18 | 0.838 | 0.780 | 0.657 | 0.494 | 0.406 |
| 24 | 0.982 | 0.889 | 0.770 | 0.641 | 0.703 |

TABLE 7

| Hrs | TriBac blend with Chemicals | TriBac blend without Chemicals | *B. coagulans* Potency | *B. subtilis* | *B. clausii* |
|---|---|---|---|---|---|
| | 2 Billion | 2 Billion | 2 Billion | 2 Billion | 2 Billion |
| 6 | 23 | 19 | 12 | 15 | 12 |
| 12 | 54 | 53 | 17 | 17 | 19 |
| 18 | 96 | 87 | 31 | 21 | 28 |
| 24 | 122 | 108 | 65 | 28 | 59 |

As shown in Table 7, the colony count of the combination probiotic composition with the chemicals is 1.87X count for CFU wherein 'X' is the maximum growth attained by any one of the bacteria (herein *Bacillus coagulans* SNZ 1969 present individually after 24 hours) showing synergy among strains with chemicals.

3D. Spinach

Spinach 3% with 1% sugar was taken as an experimental medium. 2 billion potencies of each organism was inoculated into the medium and incubate for 24 hrs. During the incubation, samples were withdrawn at the interval of 6, 12, 18 and 24 hrs and proceed further for OD measurement at 600 nm and CFU count.

Figure 6A:
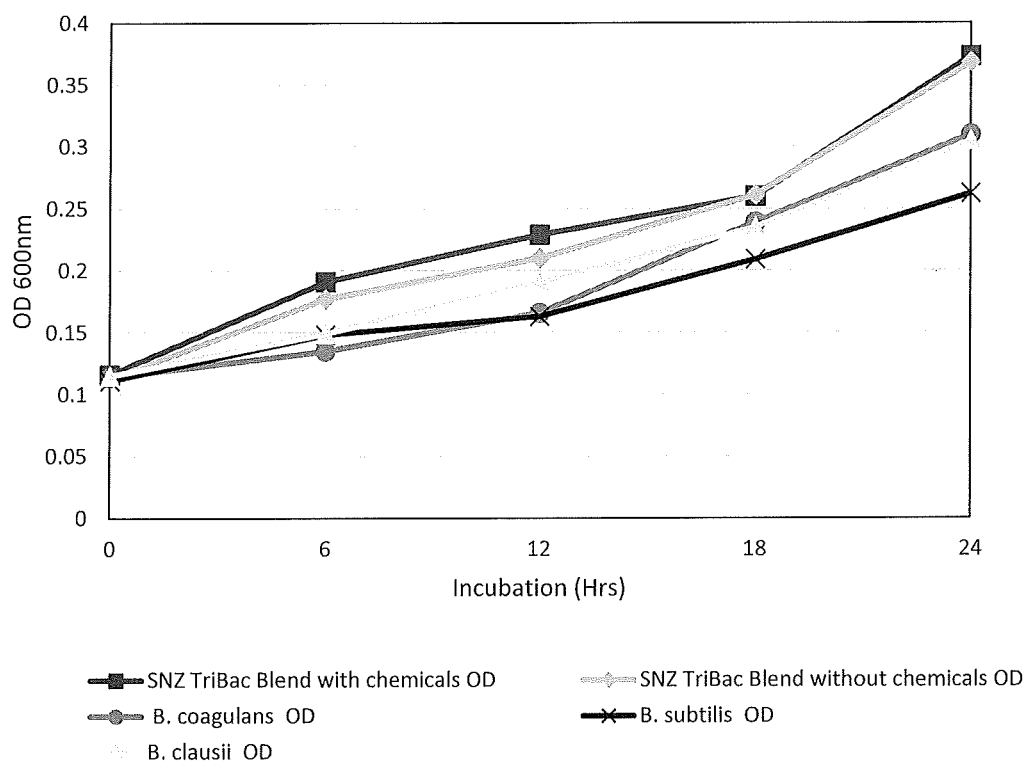
FIG. 6A depicts Comparative growth (at OD600) for SNZ TriBac Blend (with and without chemicals) as against individual strains for digestion of Spinach based media.

Table 8 shows the Growth profile (OD600) of combination TriBac blend in comparison with individual bacteria for digestion of spinach based media (corresponding FIG. 6A).

TABLE 8

| Hrs/ | TriBac blend with Chemicals | TriBac blend without Chemicals | *B. coagulans* Potency | *B. subtilis* | *B. clausii* |
|---|---|---|---|---|---|
| | 2 Billion | 2 Billion | 2 Billion | 2 Billion | 2 Billion |
| 6 | 0.191 | 0.177 | 0.135 | 0.148 | 0.149 |
| 12 | 0.229 | 0.210 | 0.166 | 0.163 | 0.190 |
| 18 | 0.260 | 0.261 | 0.239 | 0.209 | 0.235 |
| 24 | 0.373 | 0.368 | 0.310 | 0.262 | 0.305 |

Figure 6B:
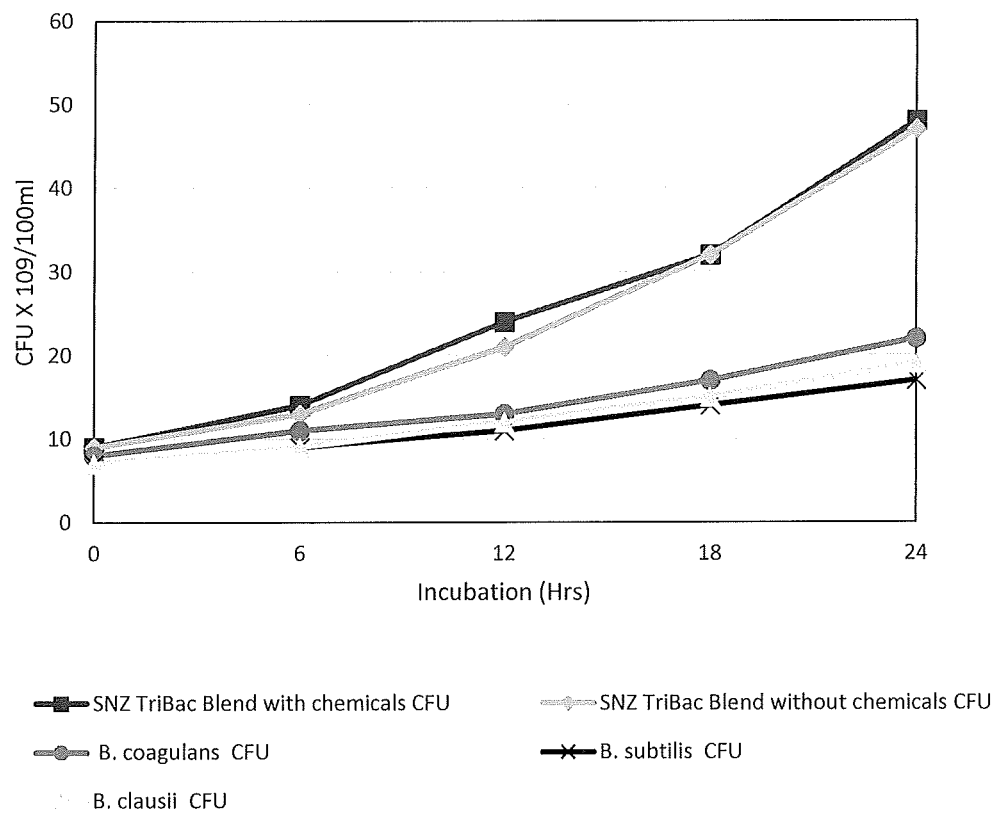
FIG. 6B depicts Comparative growth (plate count CFU/ml) for SNZ TriBac Blend (with and without chemicals) as against individual strains for digestion of Spinach based media.

Table 9 shows the Growth profile (billion CFU/100 ml) of combination TriBac blend in comparison with individual bacteria for digestion of spinach based media (corresponding FIG. 6B). As shown in Table 9, the colony count of the combination probiotic composition with the chemicals is 2.18X count for CFU wherein 'X' is the maximum growth attained by any one of the bacteria (herein *Bacillus coagulans* SNZ 1969 present individually after 24 hours) showing synergy among strains with chemicals.

TABLE 9

| Hrs/ | TriBac blend with Chemicals | TriBac blend without Chemicals | B. coagulans | B. subtilis | B. clausii |
|---|---|---|---|---|---|
| | | | Potency | | |
| | 2 Billion | 2 Billion | 2 Billion | 2 Billion | 2 Billion |
| 6 | 14 | 13 | 11 | 9 | 9 |
| 12 | 24 | 21 | 13 | 11 | 12 |
| 18 | 32 | 32 | 17 | 14 | 15 |
| 24 | 48 | 47 | 22 | 17 | 19 |

In conclusion, all the 4 food varieties Pigeon Pea (i.e. Tur Dal), Wheat Flour, Meat Powder (beef extract), and Spinach showed enhanced growth which is at least double as a blend with component chemicals as described above showing that the combination of probiotic composition comprising *Bacillus coagulans* SNZ 1969, *Bacillus subtilis* SNZ 1972, *Bacillus clausii* SNZ 1971 with the presence of magnesium stearate, magnesium hydroxide and simethicone has the capability to thrive and digest all complex vegetable and non-vegetable diets thus helping in maintaining good digestion while removing other ailments of gastrointestinal tract like diarrhoea, constipation, gas etc. In particular, the composition as described herein comprising combination of *Bacillus coagulans* SNZ 1969, *Bacillus subtilis* SNZ 1972, and *Bacillus clausii* SNZ 1971 even without the presence of magnesium stearate, magnesium hydroxide and simethicone shows synergism in growth, digestion and subsequently aiding in reduction of gas and thereby increase in gastrointestinal microbial count of pro-biotic bacterial population.

3E. Acid Profile

The major metabolic function of the colonic microflora is the fermentation of non-digestible carbohydrates, which are key sources of energy in the colon. These non-digestible carbohydrates include large polysaccharides (i.e., resistant starches, pectins, and cellulose) and some oligosaccharides that escape digestion, as well as unabsorbed sugars and alcohols. The primary metabolic endpoint of this fermentation is the generation of short-chain fatty acids. A fundamental role of short-chain fatty acids in colonic physiology is their trophic effect on the intestinal epithelium. All three major short-chain fatty acids (acetate, propionate, and butyrate) stimulate epithelial cell proliferation and differentiation in the colon in-vivo, whereas butyrate inhibits cell proliferation and stimulates cell differentiation in-vitro. Therefore, short-chain fatty acids appear to play an essential role in the control of epithelial cell proliferation and differentiation in the colon. In addition, recent studies have revealed further effects of butyrate on the intestinal barrier function. The short-chain fatty acids (SCFA), mainly acetate, propionate and butyrate, may lead to inhibition of pathogenic bacteria, stimulation of the immune system, prevention of colon cancer development, improving mineral absorption, reducing incidence of gastrointestinal diseases and improving blood lipid profile.

Figure 7:
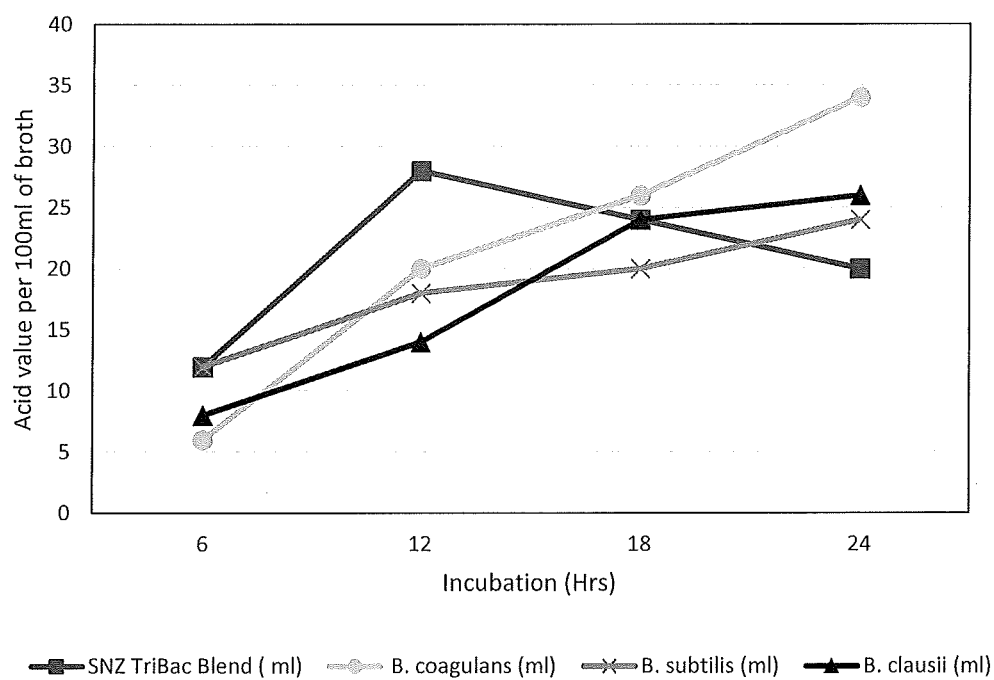
FIG. 7 depicts Consumption of short chain fatty acids by the combination probiotic composition SNZ TriBac Blend in comparison with individual bacterial strains.

The observed efficacy of the combination pro-biotic composition (TriBac) was found to be always superior to individual strains in digestion of complex veg and non veg food. Even the blend has the ability to produce more short chain fatty acids as compared to individual strains and these SCFA acts as an energy source for the growth of bacteria and for proper functioning of colon cells in intestine. The graph (FIG. 7) shows these bacteria grow at a high rate consuming these SCFA showing a steep decrease in the acid profile of the blend.

EXAMPLE 4

Synergistic Growth Efficiency at Different Concentrations of Constituent Probiotics in the Formulation with or without Chemical Constituents To check the synergy, bacterial strains *B. coagulans* SNZ 1969, *B. subtilis* SNZ 1972 and *B. clausii* SNZ 1971 were grown as a combination of 3 bacterial strains at different concentrations (provided in the Table 10 below) in a formulation with the chemicals magnesium stearate, magnesium hydroxide and simethicone. At the same time, combination of the said 3 bacterial strains *B. coagulans* SNZ 1969, *B. subtilis* SNZ 1972 and *B. clausii* SNZ 1971 at different concentrations (provided in the Table 10 below) in a formulation without the chemicals magnesium stearate, magnesium hydroxide and simethicone at equal potency in presence of the same working medium. The medium composed of 2% glucose as the carbon source, 0.5% peptone as the nitrogen source, yeast extract (0.5%) as growth factor, $KH_2PO_4$ (5 mg/100 ml) and $MgSO_4$ (1 mg/100 ml).

Table 10 shows TriBac Blend with different concentrations with and without chemicals.

TABLE 10

| Component | TriBac Blend (T1) (in Billion) | | TriBac Blend (T2) (in Billion) | | TriBac Blend (T3) (in Billion) | |
|---|---|---|---|---|---|---|
| | With chemicals | Without chemicals | With chemicals | Without chemicals | With chemicals | Without chemicals |
| B. coagulans | 1.4 | 1.4 | 0.95 | 0.95 | 0.5 | 0.5 |
| B. subtilis | 0.5 | 0.5 | 0.95 | 0.95 | 1.4 | 1.4 |
| B. clausii | 0.1 | 0.1 | 0.1 | 0.1 | 0.1 | 0.1 |
| Magnesium Stearate | 20 mg | — | 20 mg | — | 20 mg | — |
| Magnesium Hydroxide | 150 mg | — | 150 mg | — | 150 mg | — |
| Simethicone | 25 mg | — | 25 mg | — | 25 mg | — |

Figure 8:
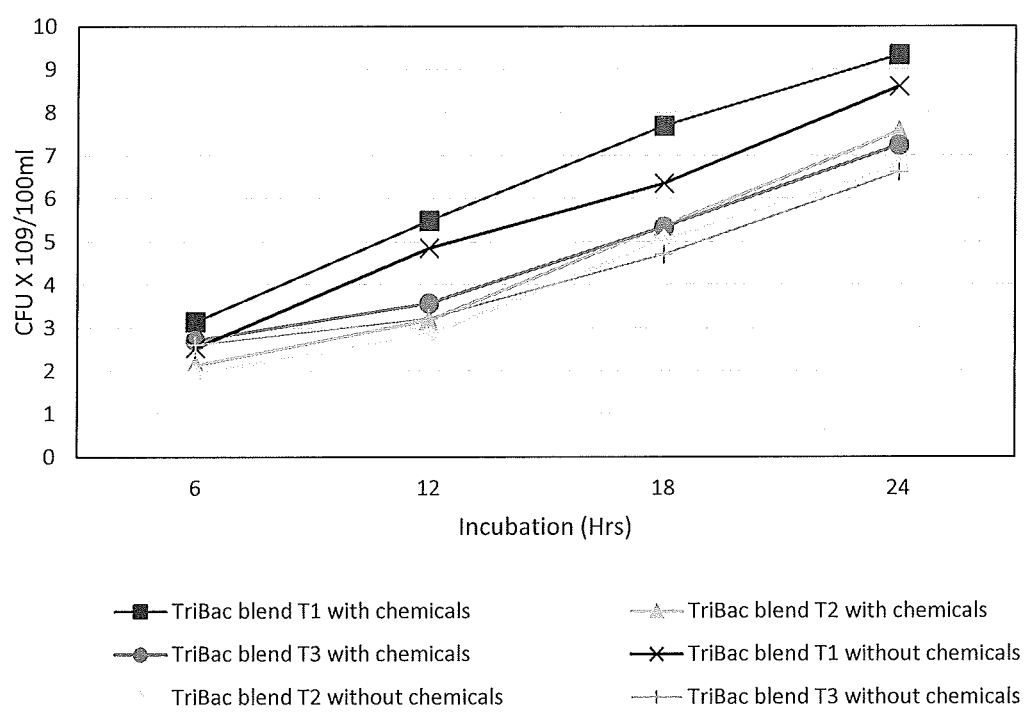
FIG. 8 depicts a Comparative growth curve of TriBac Blends T1, T2 and T3 with and without chemicals. TriBac Blend T1 with chemicals showed the highest growth efficiency as compared to other two blends T2 and T3 with chemicals. It is also confirmed that all the TriBac blends T1, T2, T3 without the chemical components showed comparatively significantly reduced growth rates to that of the respective blends with the chemical components.

The growth was observed based on OD value. Spectrophotometric $OD_{600}$ data gives total no. of viable & dead cells in the culture while plate count method specifically shows count of viable cells. With reference to FIG. 8, the growth curve observed for the TriBac blend T1 with chemicals had the highest growth efficiency as compared to other two blends (i.e TriBac Blend T2 and TriBac Blend T3 with or without chemicals). Nonetheless, the growth rate was significantly higher in case of TriBac blends T1, T2, T3 with the chemical components as against the same blends without chemical components (see, Tables 11 and 12 below).

Table 11 shows growth profile of individual strains and combination probiotic composition of SNZ-TriBac (equal potency) based on spectrophotometric readings.

EXAMPLE 5

Comparative Growth with and without Chemical Components in the Probiotic Components To check the effect of chemical ingredients wherein particularly magnesium stearate, magnesium hydroxide and simethicone have been used in the intended combination probiotic composition, each of the bacterial strains *B. coagulans* SNZ 1969, *B. subtilis* SNZ 1972 & *B. clausii* SNZ 1971 were separately and individually grown each at a concentration of 2 billion added with the chemical components

TABLE 11

| | Growth profile (OD at 600 nm) without chemicals | | | | | | Growth profile (OD at 600 nm) with chemicals | | | | | |
|---|---|---|---|---|---|---|---|---|---|---|---|---|
| Hours | T1 | pH | T2 | pH | T3 | pH | T1 | pH | T2 | pH | T3 | pH |
| 0 | — | 9.42 | — | 9.42 | — | 9.42 | — | 6.20 | — | 6.20 | — | 6.20 |
| 6 | 0.110 | 9.29 | 0.190 | 9.32 | 0.129 | 9.20 | 0.124 | 5.39 | 0.230 | 5.85 | 0.190 | 5.68 |
| 12 | 0.233 | 5.38 | 0.201 | 6.27 | 0.201 | 5.76 | 0.490 | 5.17 | 0.243 | 5.08 | 0.244 | 5.18 |
| 18 | 0.259 | 5.25 | 0.363 | 5.36 | 0.231 | 5.18 | 0.732 | 4.95 | 0.421 | 5.07 | 0.593 | 5.05 |
| 24 | 0.286 | 4.91 | 0.392 | 5.03 | 0.242 | 7.35 | 0.763 | 4.34 | 0.668 | 4.10 | 0.795 | 4.24 |

Table 12 shows growth profile of individual strains and combination probiotic composition of SNZ TriBac™ (equal potency) based on plate count.

magnesium stearate (20 mg), magnesium hydroxide (150 mg) and simethicone (25 mg) in a formulation and without the chemicals both in the presence of the same working

TABLE 12

| | Growth profile (Billion CFU/100 ml) with chemicals* | | | | | | Growth profile (Billion CFU/100 ml) without chemicals* | | | | | |
|---|---|---|---|---|---|---|---|---|---|---|---|---|
| Hours | T1* | pH | T2* | pH | T3* | pH | T1* | pH | T2* | pH | T3* | pH |
| 0 | — | 9.42 | — | 9.42 | — | 9.42 | — | 6.20 | — | 6.20 | — | 6.20 |
| 6 | 3.14 | 9.29 | 2.13 | 9.32 | 2.71 | 9.20 | 2.53 | 5.39 | 1.93 | 5.85 | 2.61 | 5.68 |
| 12 | 5.49 | 5.38 | 3.18 | 6.27 | 3.57 | 5.76 | 4.85 | 5.17 | 2.84 | 5.08 | 3.22 | 5.18 |
| 18 | 7.69 | 5.25 | 5.37 | 5.36 | 5.35 | 5.18 | 6.35 | 4.95 | 5.04 | 5.07 | 4.71 | 5.05 |
| 24 | 9.34 | 4.91 | 7.56 | 5.03 | 7.24 | 7.35 | 8.6 | 4.34 | 6.74 | 4.10 | 6.62 | 4.24 |

The colony forming unit readings of combination probiotic composition, namely TriBac Blend T1 with chemicals comprising 1.4 billion *B. coagulans* SNZ 1969, 0.5 billion *B. subtilis* SNZ 1972, 0.1 billion *B. clausii* SNZ 1971, 20 mg magnesium stearate, 150 mg magnesium hydroxide and 25 mg simethicone is the most preferred combination probiotic composition with chemicals.

medium (Tables 13 and 14 below). The medium composed of 2% glucose as the carbon source, 0.5% peptone as the nitrogen source, yeast extract (0.5%) as growth factor, $KH_2PO_4$ (5 mg/100 ml) and $MgSO_4$ (1 mg/100 ml). The results obtained are shown below:

Table 13 shows Growth profile (OD at 600 nm) with and without chemicals of each individual bacterial strains.

TABLE 13

| Hours | B. coagulans (2Billion) | pH | B. cogulans (2billion) + chemicals | pH | B. subtilis (2Billion) | pH | B. subtilis (2billion) + chemicals | pH | B. clausii (2Billion) | pH | B. clausii (2billion) + chemicals | pH |
|---|---|---|---|---|---|---|---|---|---|---|---|---|
| 0 | — | 6.20 | — | 9.42 | — | 6.20 | — | 9.42 | — | 6.20 | — | 9.42 |
| 6 | 0.022 | 6.12 | 0.003 | 9.32 | 0.083 | 5.08 | 0.007 | 9.32 | 0.006 | 6.10 | 0.017 | 9.36 |
| 12 | 0.081 | 4.19 | 0.212 | 9.14 | 0.212 | 5.31 | 0.114 | 9.14 | 0.140 | 4.52 | 0.239 | 5.23 |
| 18 | 0.139 | 4.20 | 0.371 | 7.62 | 0.318 | 5.37 | 0.565 | 7.62 | 0.291 | 4.60 | 0.376 | 5.09 |
| 24 | 0.179 | 4.24 | 0.507 | 5.22 | 0.358 | 4.62 | 0.627 | 5.22 | 0.450 | 5.09 | 0.683 | 4.89 |

Table 14 shows Growth profile (billion CFU/100/ml) with and without chemicals of each individual bacterial strains.

TABLE 14

| Hours | B. coagulans (2Billion) | pH | B. cogulans (2billion) + chemicals | pH | B. subtilis (2Billion) | pH | B. subtilis (2billion) + chemicals | pH | B. clausii (2Billion) | pH | B. clausii (2billion) + chemicals | pH |
|---|---|---|---|---|---|---|---|---|---|---|---|---|
| 0 | — | 6.20 | — | 9.42 | — | 6.20 | — | 9.42 | — | 6.20 | — | 9.42 |
| 6 | 2.1 | 6.12 | 2.3 | 9.32 | 2.9 | 5.08 | 3.1 | 9.32 | 1.8 | 6.10 | 1.9 | 9.36 |
| 12 | 3.9 | 4.19 | 4.2 | 9.14 | 4.8 | 5.31 | 5.4 | 6.89 | 2.6 | 4.52 | 3.1 | 5.23 |
| 18 | 4.9 | 4.20 | 5.7 | 7.62 | 6.1 | 5.37 | 6.8 | 7.62 | 4.5 | 4.60 | 5 | 5.09 |
| 24 | 6.1 | 4.24 | 6.6 | 5.22 | 7.6 | 4.62 | 8.2 | 5.22 | 6 | 5.09 | 6.3 | 4.89 |

Thus it is established that the growth of all of the individual bacterial strains in presence of chemicals or the combined probiotic compositions of the TriBac blends T1, T2 and T3 above always contributes in substantially higher growth rates for the same time interval (as exemplified at $6^{th}$, $12^{th}$, $18^{th}$ and $24^{th}$ hours) as compared with the bacteria (individual or in combination) without the chemicals for the same respective time intervals.

It is expected the administration of TriBac blend compositions with added chemical components as described above (Table 10) will provide synergistic effects in a human, such as increased growth of one or more of B. coagulans, B. subtilis, or B. clausii. In particular, the probiotic blend, in particular the deposited strains listed herein, will treat or prevent indigestion, constipation, diarrhea and gas formation in the stomach. Symptoms associated with these conditions will be improved, such as improved digestion.

Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entireties for all purposes.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

We claim:

1. A probiotic blend composition comprising *Bacillus coagulans, Bacillus subtilis,* and *Bacillus clausii* in combination with magnesium stearate, magnesium hydroxide, and simethicone, wherein the amount of B. coagulans is between 0.5 billion to 1.5 billion CFUs, the amount of B. clausii is between 0.1 billion to 0.5 billion CFUs, and the amount of B. subtilis is between 0.1 billion to 1.5 billon CFUs.

2. The probiotic blend composition of claim 1, wherein the probiotic blend composition contains a total dosage of 2 billion CFUs.

3. The probiotic blend composition of claim 1, wherein the amount of B. coagulans is 1.4 billion CFUs, the amount of B. subtilis is 0.1 billion CFUs, and the amount of B. clausii is 0.5 billion CFUs.

4. The probiotic blend of claim 1, wherein B. coagulans is SNZ 1969 having accession number MTCC 5724, B. subtilis is SNZ 1972 having accession number MTCC 5981 and B. clausii is SNZ 1971 having accession number MTCC 5980.

5. A method for improving digestion of complex carbohydrates, proteins and fibers in a human, comprising the steps of:
providing a probiotic blend composition comprising B. coagulans, B. subtilis, and B. clausii in combination with magnesium stearate, magnesium hydroxide, and simethicone, wherein the amount of B. coagulans is between 0.5 billion to 1.5 billion CFUs, the amount of

*B. clausii* is between 0.1 billion to 0.5 billion CFUs, and the amount of *B. subtilis* is between 0.1 billion to 1.5 billion CFUs; and administering to the human the probiotic blend composition.

6. The method of claim 5, wherein the probiotic blend composition contains a total dosage of 2 billion CFUs.

7. The method of claim 5, wherein the amount of *B. coagulans* is 1.4 billion CFUs, the amount of *B. clausii* is 0.5 billion CFUs, and the amount of *B. subtilis* is 0.1 billion CFUs.

8. The method of claim 5, wherein *B. coagulans* is SNZ 1969, *B. subtilis* is SNZ 1972, and *B. clausii* is SNZ 1971.

* * * * *